United States Patent [19]

Kimata et al.

[11] Patent Number: 5,286,738
[45] Date of Patent: * Feb. 15, 1994

[54] TRIAZOLE COMPOUND AND INSECTICIDE

[75] Inventors: Toshiya Kimata; Shunji Hayashi; Satoshi Yamanaka; Sayoko Kawaguchi; Kazuhiro Kojima, all of Tokyo, Japan

[73] Assignee: S.D.S. Biotech K.K., Tokyo, Japan

[30] Foreign Application Priority Data

[ * ] Notice: The portion of the term of this patent subsequent to Nov. 6, 2008 has been disclaimed.

[21] Appl. No.: 772,360

[22] PCT Filed: Nov. 6, 1991

[86] PCT No.: PCT/JP91/00300
§ 371 Date: Mar. 6, 1991
§ 102(e) Date: Mar. 6, 1991

[87] PCT Pub. No.: WO91/13879
PCT Pub. Date: Apr. 17, 1991

Mar. 6, 1990 [JP] Japan .................... 2-52708

[51] Int. Cl.$^5$ ................ A01N 43/653; C07D 249/12; C07D 401/08

[52] U.S. Cl. .................... 514/384; 514/340; 546/276; 548/264.2; 548/264.4
[58] Field of Search ............... 514/340, 384; 546/276; 548/264.2, 264.4

[56] References Cited

U.S. PATENT DOCUMENTS 3,794,661  2/1974  Bochner et al. ............ 548/264.4
5,155,124  10/1992  Kinata et al. ............... 514/384

FOREIGN PATENT DOCUMENTS 0036711  9/1981  European Pat. Off.
0213718  11/1987  European Pat. Off.
0337815  10/1989  European Pat. Off.

*Primary Examiner*—Patricia L. Morris
*Attorney, Agent, or Firm*—Sughrue, Mion, Zinn, Macpeak & Seas

[57] ABSTRACT

A triazole compound of the formula (I):

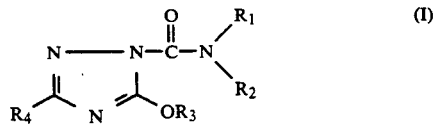

and an insecticide comprising the same as the active ingredient.

6 Claims, No Drawings

TRIAZOLE COMPOUND AND INSECTICIDE

This application is a continuation of PCT/JP91/00300, filed Mar. 6, 1990.

TECHNICAL FIELD

The present invention relates to a triazole compound represented by the following formula (I) and an insecticide containing said compound as an active ingredient.

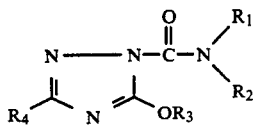

[wherein
$R_1$ represents hydrogen or a lower alkyl group (preferably an alkyl group having 1 to 2 carbon atoms);
$R_2$ represents a lower alkyl group (preferably an alkyl group having 1 to 2 carbon atoms);
$R_3$ represents an alkyl group (preferably an alkyl group having 1 to 12 carbon atoms), an alkenyl group (preferably an alkenyl group having 1 to 12 carbon atoms), a cycloalkylmethyl group (preferably a cycloalkylmethyl group having 4 to 7 carbon atoms), a haloalkyl group (preferably a haloalkyl group having 1 to 12 carbon atoms), an alkyl group (preferably an alkyl group having 1 to 6 carbon atoms) substituted with a phenyl group (which may be also substituted with a halogen atom, an alkyl group (preferably an alkyl group having 1 to 6 carbon atoms), a haloalkyl group (preferably a haloalkyl group having 1 to 6 carton atoms), an alkoxy group (preferably an aloxy group having 1 to 6 carbon atoms) or a haloalkoxy group (preferably a haloalkyl group having 1 to 6 carbon atoms)), an alkenyl group (preferably an alkenyl group having 3 to 6 carbon atoms), an oxyalkyl group (preferably a hydroxyalkyl group having 1 to 6 carbon atoms), a thioxyalkyl group (preferably a thioxyalkyl group having 1 to 6 carbon atoms) or a carbonylalkyl group (preferably a carbonylalkyl group having 1 to 6 carbon atoms), an alkyl group (preferably an alkyl group having 1 to 6 carbon atoms) substituted with an alkoxy group (preferably an alkoxy group having 1 to 6 carbon atoms) or an alkylthio group (preferably an alkylthio group having 1 to 6 carbon atoms), an alkyl group (preferably an alkyl group having 1 to 6 carbon atoms) substituted with an alkylsulfinyl group (preferably an alkylsulfinyl group having 1 to 6 carbon atoms) or an alkylsulfonyl group (preferably an alkylsulfonyl group having 1 to 6 carbon atoms), an alkyl group (preferably an alkyl group having 1 to 6 carbon atoms) substituted with an α, β- or γ-pyridyl group, an alkyl group (preferably an alkyl group having 1 to 6 carbon atoms) substituted with an α- or β-thionyl group (which may be also substituted with a halogen atom), an alkyl group (preferably an alkyl group having 1 to 6 carbon atoms) substituted with a cyano group or an alkyl group (preferably an alkyl group having 1 to 6 carbon atoms) substituted with an alkoxycarbonyl group (preferably an alkoxycarbonyl group having 2 to 7 carbon atoms),
$R_4$ represents

(where $R_5$, $R_6$ and $R_7$ represent the same or different lower alkyl groups (preferably alkyl groups having 1 to 3 carbon atoms), or in some cases, two groups of $R_5$, $R_6$ and $R_7$ can form a carbon ring (preferably a carbon ring having 3 to 5 carbon atoms))].

More particularly, the present invention relates to the triazole compound represented by the above formula (I) (hereinafter called the present compound) and an insecticidal composition for agriculture and horticulture, and for a prevention of epidemics, and having a strong insecticidal activity against Hemiptera, Diptera, Nematoidea, Pseudonematoidea, comprising the present compound as the active ingredient.

BACKGROUND ART 3-t-butyl-1-(N-N-dimethylcarbamoyl)-1,2,4-triazole type compounds exhibiting an insecticidal activity are known in the art, as disclosed, for example, in Japanese Unexamined Patent Publications (Kokai) Nos. 52-122624, 52-122626, 55-38387, and 62-70365.

Nevertheless, these compounds do not have a satisfactory insecticidal spectrum and insecticidal performance. In particular, it should be noted that these compounds have not been practically applied due to an insufficient effect in practical application or an occurrence of phytotoxicity when highly effective. Further, the 5-position substituted with triazole is an alkylthio, alkylthioalkylthio, or alkoxycarbonylalkylthio group which is completely different from the $OR_3$ (where $R_3$ is as defined above) of the 5-position substituent of the present compound.

DISCLOSURE OF THE INVENTION

Therefore, the present invention is intended to develop a novel insecticidal compound, which is a novel substance not known in the prior art of 3-t-butyl-1-(N,N-dimethylcarbamoyl)-1,2,4-triazole type compounds, and having an excellent insecticidal spectrum and insecticidal performance, particularly an insecticidal compound which has an extremely strong insecticidal activity against Hemiptera, Diptera, Nematoidea, Pseudonematoidea, and is safe for use on crops, and an insecticide comprising the same as the active ingredient.

Other objects and advantages of the present invention will be apparent from the following description.

In accordance with the present invention, there are provided the compound represented by the above formula (I) and the insecticide comprising said compound as the active ingredient.

The present inventors found, surprisingly, that the compound represented by the above formula (I) has an excellent insecticidal spectrum and insecticidal performance, has a strong insecticidal activity, particularly against Hemiptera, Diptera, Nematoidea, Pseudonematoidea, and exhibits substantially no phytotoxicity to crops.

BEST MODE OF CARRYING OUT THE INVENTION

The present compound is a novel compound not reported in any literature. The $R_1$ to $R_4$ in the formula (I) are as defined above, but preferable examples of $R_1$, $R_2$ are (methyl, methyl), (ethyl, ethyl) and (methyl, ethyl), particularly preferably (methyl, methyl).

Representative examples of the compounds of the present invention include those as shown in Table-1.

The NMR values in the Table were measured at 60 MHz with tetramethylsilane as the internal standard in deuterochloroform, and the symbols s, d, t, q, m respectively indicate the peak patterns of singlet, doublet, triplet, quadruplet, multiplet, and br indicates a broad peak pattern.

In the following description, the compounds are shown with reference to the compound No. in the Table.

TABLE 1

(I)

| Compd. No. | $R_1$ | $R_2$ | $R_3$ | $R_4$ | Property or mp (°C.) | $^1$H-NMR |
|---|---|---|---|---|---|---|
| 1 | Me | Me | $C_2H_5$ | $CMe_3$ | Oily | δ1.30(s, 9H, t-Bu), 1.40(t, J=7Hz, 3H, Me), 3.00(s, 6H, $NMe_2$), 4.45(q, J=7Hz, 2H, $OCH_2$) |
| 2 | Me | Me | $n$-$C_3H_7$ | $CMe_3$ | " | δ1.00(t, J=7Hz, 3H, Me), 1.30(s, 9H, t-Bu), 1.6~2.0(m, 2H, $CH_2$), 3.00(s, 6H, $NMe_2$), 4.35(t, J=6Hz, 2H, $OCH_2$) |
| 3 | Me | Me | iso-$C_3H_7$ | $CMe_3$ | " | δ1.30(s, 9H, t-Bu), 1.40(d, J=6Hz, 6H, $Me_2$), 3.00(s, 6H, $NMe_2$), 4.8~5.3(m, 1H, OCH) |
| 4 | Me | Me | $n$-$C_4H_9$ | $CMe_3$ | " | δ0.8~1.1(m, 3H, Me), 1.30(s, 9H, t-Bu), 1.4~2.1(m, 4H, $(CH_2)_2$), 3.00(s, 6H, $NMe_2$), 4.40(t, J=6Hz, 2H, $OCH_2$) |
| 5 | Me | Me | iso-$C_4H_9$ | $CMe_3$ | " | δ0.95(d, J=7Hz, 6H, $Me_2$), 1.30(s, 9H, t-Bu), 1.8~2.3(m, 1H, CH), 3.00(s, 6H, $NMe_2$), 4.15(d, J=6Hz, 2H, $OCH_2$) |
| 6 | Me | Me | $n$-$C_5H_{11}$ | $CMe_3$ | " | δ0.8~1.1(m, 3H, Me), 1.30(s, 9H, t-Bu), 1.3~2.1(m, 6H, $(CH_2)_3$), 3.00(s, 6H, $NMe_2$), 4.40(t, J=6Hz, 2H, $OCH_2$) |
| 7 | Me | Me | $n$-$C_6H_{13}$ | $CMe_3$ | " | δ0.8~1.1(m, 3H, Me), 1.30(s, 9H, t-Bu), 1.2~2.1(m, 8H, $(CH_2)_4$), 3.00(s, 6H, $NMe_2$), 4.40(t, J=6Hz, 2H, $OCH_2$) |
| 8 | Me | Me | $(CH_3)_2CH(CH_2)_2$— | $CMe_3$ | Oily | δ0.95(d, J=6Hz, 6H, $Me_2$), 1.30(s, 9H, t-Bu), 1.6~2.0(m, 3H, $CH_2CH$), 3.00(s, 6H, $NMe_2$), 4.40(t, J=6Hz, 2H, $OCH_2$) |
| 9 | Me | Me | cyc-Pr—$CH_2$— | $CMe_3$ | " | δ0.2~0.8(m, 4H, cyc-Pr), 1.1~1.5(m, 1H, cyc-Pr), 1.30(s, 9H, t-Bu), 3.05(s, 6H, $NMe_2$), 4.20(d, J=7Hz, $OCH_2$) |
| 10 | Me | Me | $CH_2$=CH—$CH_2$— | $CMe_3$ | " | δ1.30(s, 9H, t-Bu), 3.00(s, 6H, $NMe_2$), 4.85(d, J=6Hz, 2H, $OCH_2$), 5.0~6.2(m, 3H, CH=$CH_2$) |
| 11 | Me | Me | $CH_3CH$=CH—$CH_2$— | $CMe_3$ | " | δ1.30(s, 9H, t-Bu), 1.75(br.d, J=5Hz, 3H, Me), 3.00(s, 6H, $NMe_2$), 4.7~5.0(m, 2H, $OCH_2$), 5.5~5.9(m, 2H, CH=CH) |
| 12 | Me | Me | $CH_2$=CH$(CH_2)_2$— | $CMe_3$ | " | δ1.30(s, 9H, t-Bu), 2.3~2.8(m, 2H, $CH_2$), 3.00(s, 6H, $NMe_2$), 4.45(t, J=7Hz, 2H, $OCH_2$), 4.8~6.1(m, 3H, CH=$CH_2$) |
| 13 | Me | Me | $(CH_3)_2C$=CH—$CH_2$— | $CMe_3$ | " | δ1.30(s, 9H, t-Bu), 1.75(s, 6H, $Me_2$), 3.00(s, 6H, $NMe_2$), 4.90(d, J=8Hz, 2H, $OCH_2$), 5.2~5.6(m, 1H, CH=) |
| 14 | Me | Me | $(CH_3)_2C$=CH$(CH_2)_2$— | $CMe_3$ | " | δ1.30(s, 9H, t-Bu), 1.70(br.d, J=3Hz, 6H, $Me_2$), 2.3~2.7(m, 2H, $CH_2$), 3.00(s, 6H, $NMe_2$), 4.30(t, J=7Hz, 2H, $OCH_2$), 4.8~5.2(m, 1H, CH=) |
| 15 | Me | Me | $(CH_2)_2OC_2H_5$ | $CMe_3$ | " | δ1.20(t, J=7Hz, 3H, Me), 1.30(s, 9H, t-Bu), 3.00(s, 6H, $NMe_2$), 3.3~3.9(m, 4H, $CH_2$, $OCH_2$), 4.4~4.6(m, 2H, $OCH_2$) |
| 16 | Me | Me | $CH_2$–benzyl | $CMe_3$ | 100~101 | δ1.30(s, 9H, t-Bu), 3.00(s, 6H, $NMe_2$), 5.40(s, 2H, $OCH_2$), 7.1~7.5(m, 5H, PhH) |
| 17 | Me | Me | $CH_2$–(2-Cl-phenyl) | $CMe_3$ | 63~64 | δ1.30(s, 9H, t-Bu), 3.00(s, 6H, $NMe_2$), 5.50(s, 2H, $OCH_2$), 7.0~7.6(m, 4H, PhH) |

TABLE 1-continued

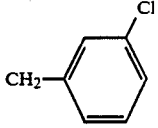

(I)

| Compd. No. | R₁ | R₂ | R₃ | R₄ | Property or mp (°C.) | ¹H-NMR |
|---|---|---|---|---|---|---|
| 18 | Me | Me | 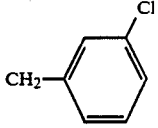 | CMe₃ | Oily | δ1.30(s, 9H, t-Bu), 3.00(s, 6H, NMe₂), 5.35(s, 2H, OCH₂), 7.1~7.5(m, 4H, PhH) |
| 19 | Me | Me | 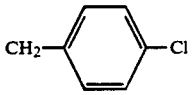 | CMe₃ | " | δ1.30(s, 9H, t-Bu), 3.00(s, 6H, NMe₂), 5.35(s, 2H, OCH₂), 7.1~7.4(m, 4H, PhH) |
| 20 | Me | Me | 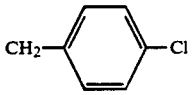 | CMe₃ | 65~67 | δ1.30(s, 9H, t-Bu), 3.00(s, 6H, NMe₂), 5.50(s, 2H, OCH₂), 6.7~7.7(m, 4H, PhH) |
| 21 | Me | Me | 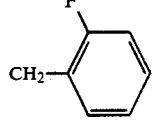 | CMe₃ | Oily | δ1.30(s, 9H, t-Bu), 3.00(s, 6H, NMe₂), 5.35(s, 2H, OCH₂), 6.7~7.5(m, 4H, PhH) |
| 22 | Me | Me | 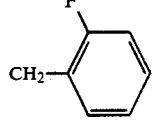 | CMe₃ | 71~73 | δ1.30(s, 9H, t-Bu), 2.40(s, 3H, Me), 3.00(s, 6H, NMe₂), 5.40(s, 2H, OCH₂), 7.0~7.5(m, 4H, PhH) |
| 23 | Me | Me | 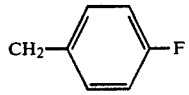 | CMe₃ | Oily | δ1.30(s, 9H, t-Bu), 2.30(s, 3H, Me), 3.00(s, 6H, NMe₂), 5.35(s, 2H, OCH₂), 6.9~7.3(m, 4H, PhH) |
| 24 | Me | Me | 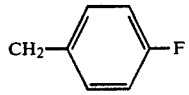 | CMe₃ | 69~71 | δ1.30(s, 9H, t-Bu), 2.95(s, 6H, NMe₂), 3.05(t, J=7Hz, CH₂), 4.55(t, J=7Hz, OCH₂), 7.15(br.s, 5H, PhH) |
| 25 | Me | Me | (CH₂)₃Cl | CMe₃ | 40~42 | δ1.30(s, 9H, t-Bu), 2.0~2.5(m, 2H, CH₂), 3.05(s, 6H, NMe₂), 3.65(t, J=6Hz, 2H, CH₂Cl), 4.50(t, J=6Hz, 2H, OCH₂) |
| 26 | Me | Me | (CH₂)₄Cl | CMe₃ | Oily | δ1.30(s, 9H, t-Bu), 1.8~2.2(m, 4H, CH₂CH₂), 3.05(s, 6H, NMe₂), 3.4~3.7(m, 2H, CH₂Cl), 4.3~4.6(m, 2H, OCH₂) |
| 27 | Me | Me | CH₂SCH₃ | CMe₃ | 101~103 | δ1.35(s, 9H, t-Bu), 2.35(s, 3H, SMe), 3.00(s, 6H, NMe₂), 4.80(s, 2H, OCH₂) |
| 28 | Me | Me | (CH₂)₂SCH₃ | CMe₃ | Oily | δ1.30(s, 9H, t-Bu), 2.15(s, 3H, SMe), 2.85(t, J=7Hz, 2H, CH₂S), 3.00(s, 6H, NMe₂), 4.50(t, J=7Hz, 2H, OCH₂) |
| 29 | Me | Me | (CH₂)₂SC₂H₅ | CMe₃ | " | δ1.30(s, 9H, t-Bu), 1.30(t, J=7Hz, 3H, Me), 2.5~2.9(m, 4H, CH₂SCH₂), 3.05(s, 6H, NMe₂), 4.50(t, J=7Hz, 2H, OCH₂) |
| 30 | Me | Me | CH₂SOCH₃ | CMe₃ | 206~208 | δ1.40(s, 9H, t-Bu), 2.80(s, 3H, SOMe), 3.00(s, 6H, NMe₂), 4.80(d, J=3Hz, 2H, OCH₂) |
| 31 | Me | Me | (CH₂)₂SOCH₃ | CMe₃ | 93~96 | δ1.30(s, 9H, t-Bu), 2.70(s, 3H, SOMe), 3.00(s, 6H, NMe₂), 2.9~3.2(m, 2H, CH₂SO), 4.80(t, J=6Hz, 2H, OCH₂) |
| 32 | Me | Me | (CH₂)₂SOC₂H₅ | CMe₃ | 78~82 | δ1.30(s, 9H, t-Bu), 1.35(t, J=7Hz, 3H, Me), 2.80(q, J=7Hz, 2H, SOCH₂), 3.00(s, 6H, NMe₂), 3.10(t, J=6Hz, 2H, CH₂SO), 4.80(t, J=6Hz, 2H, OCH₂) |
| 33 | Me | Me | CH₂SO₂CH₃ | CMe₃ | 162~164 | δ1.40(s, 9H, t-Bu), 3.00(s, 6H, NMe₂), 3.15(s, 3H, SO₂Me), 5.00(s, 2H, OCH₂) |
| 34 | Me | Me | (CH₂)₂SO₂CH₃ | CMe₃ | 154~157 | δ1.30(s, 9H, t-Bu), 3.05(s, 9H, NMe₂, SO₂Me), |

TABLE 1-continued

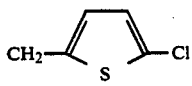
(I)

| Compd. No. | R₁ | R₂ | R₃ | R₄ | Property or mp (°C.) | ¹H-NMR |
|---|---|---|---|---|---|---|
| | | | | | | 3.40(t, J=6Hz, 2H, CH₂SO₂), 4.80(t, J=6Hz, 2H, OCH₂) |
| 35 | Me | Me | (CH₂)₂SO₂C₂H₅ | CMe₃ | 143~144 | δ1.30(s, 9H, t-Bu), 1.40(t, J=7Hz, 3H, Me), 3.05(s, 6H, NMe₂), 3.20(q, J=7Hz, 2H, SO₂CH₂), 3.40(t, J=6Hz, 2H, CH₂SO₂), 4.80(t, J=6Hz, 2H, OCH₂) |
| 36 | Me | Me | 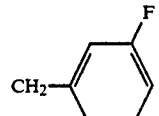 | CMe₃ | Oily | δ1.30(s, 9H, t-Bu), 3.00(s, 6H, NMe₂), 5.40(s, 2H, OCH₂), 6.65(d, J=4Hz, 1H, Thiophene H), 6.90(d, J=4Hz, 1H, Thiophene H) |
| 37 | Me | Me | 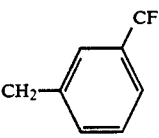 | CMe₃ | 79~81 | δ1.30(s, 9H, t-Bu), 3.00(s, 6H, NMe₂), 5.40(s, 2H, OCH₂), 6.7~7.3(m, 4H, PhH) |
| 38 | Me | Me | 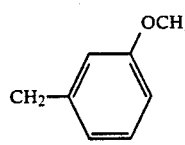 | CMe₃ | Oily | δ1.30(s, 9H, t-Bu), 3.00(s, 6H, NMe₂), 5.40(s, 2H, OCH₂), 7.2~7.8(m, 4H, PhH) |
| 39 | Me | Me | 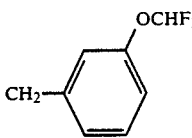 | CMe₃ | " | δ1.30(s, 9H, t-Bu), 3.00(s, 6H, NMe₂), 3.70(s, 3H, OMe), 5.35(s, 2H, OCH₂), 6.6~7.2(m, 4H, PhH) |
| 40 | Me | Me | 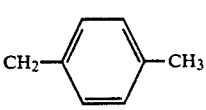 | CMe₃ | " | δ1.30(s, 9H, t-Bu), 3.00(s, 6H, NMe₂), 5.40(s, 2H, OCH₂), 6.40(t, J=72Hz, 1H, OCHF₂), 6.7~7.4(m, 4H, PhH) |
| 41 | Me | Me | 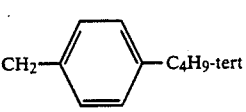 | CMe₃ | " | δ1.30(s, 9H, t-Bu), 2.30(s, 3H, Me), 3.00(s, 6H, NMe₂), 5.35(s, 2H, OCH₂), 7.00(d, J=8Hz, 2H, PhH), 7.25(d, J=8Hz, 2H, PhH) |
| 42 | Me | Me | 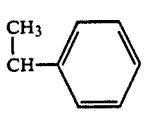 | CMe₃ | Oily | δ1.30(s, 18H, t-Bu₂), 3.00(s, 6H, NMe₂), 5.35(s, 2H, OCH₂), 7.25(s, 4H, PhH) |
| 43 | Me | Me | 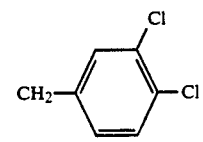 | CMe₃ | 67~69 | δ1.30(s, 9H, t-Bu), 1.70(d, J=7Hz, 3H, Me), 2.95(s, 6H, NMe₂), 5.95(q, J=7Hz, 1H, OCH), 7.0~7.5(m, 5H, PhH) |
| 44 | Me | Me | 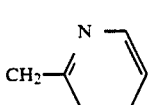 | CMe₃ | 93~94 | δ1.30(s, 9H, t-Bu), 3.00(s, 6H, NMe₂), 5.30(s, 2H, OCH₂), 7.1~7.6(m, 3H, PhH) |
| 45 | Me | Me |  | CMe₃ | 69~72 | δ1.30(s, 9H, t-Bu), 3.00(s, 6H, NMe₂), 5.50(s, 2H, OCH₂), 6.9~7.2(m, 1H, PyH), 7.3~7.8(m, 2H, PyH), 8.4(br.d, J=5Hz, 1H, PyH) |

TABLE 1-continued $$\underset{R_4}{\overset{N}{\underset{\|}{\text{—}}}}\underset{N}{\overset{\text{—}}{\underset{\|}{\text{N}}}}\underset{\text{OR}_3}{\overset{\text{O}}{\underset{\|}{\text{—C—N}}}}\overset{R_1}{\underset{R_2}{}}$$ (I)

| Compd. No. | $R_1$ | $R_2$ | $R_3$ | $R_4$ | Property or mp (°C.) | $^1$H-NMR |
|---|---|---|---|---|---|---|
| 46 | Me | Me | CH$_2$-(3-pyridyl) | CMe$_3$ | 89~91 | δ1.30(s, 9H, t-Bu), 3.00(s, 6H, NMe$_2$), 5.40(s, 2H, OCH$_2$), 7.2(dd, J=5, 7Hz, 1H, PyH), 7.6~7.9(m, 1H, PyH), 8.4(dd, J=1.5, 5Hz, 1H, PyH), 8.6(br.s, 1H, PyH) |
| 47 | Me | Me | CH$_2$-(4-pyridyl) | CMe$_3$ | 81~82 | δ1.30(s, 9H, t-Bu), 3.05(s, 6H, NMe$_2$), 5.40(s, 2H, OCH$_2$), 7.2~7.4(m, 2H, PyH), 8.4~8.6(m, 2H, PyH) |
| 48 | Me | Me | CH$_2$—C$_6$H$_{11}$-cyc | CMe$_3$ | Oily | δ1.30(s)0.7~2.1(m)(20H, t-Bu, cyc-Hex), 3.00(s, 6H, NMe$_2$), 4.20(d, J=6Hz, 2H, OCH$_2$) |
| 49 | Me | Me | CH$_2$-(2-thienyl) | CMe$_3$ | 88~90 | δ1.30(s, 9H, t-Bu), 3.00(s, 6H, NMe$_2$), 5.40(s, 2H, OCH$_2$), 7.0~7.5(m, 3H, Thiophene H) |
| 50 | H | Me | CH$_2$-Ph | CMe$_3$ | 86~89 | δ1.30(s, 9H, t-Bu), 2.85(d, J=5Hz, 3H, NMe), 5.45(s, 2H, OCH$_2$), 6.6(br.s, 1H, NH), 7.1~7.5(m, 5H, PhH) |
| 51 | Me | Me | CH$_2$-Ph | CMe$_2$Et | Oily | δ0.75(t, J=7Hz, 3H, Me), 1.25(s, 6H, CMe$_2$), 1.65(q, J=7Hz, 2H, CH$_2$), 3.00(s, 6H, NMe$_2$), 5.40(s, 2H, OCH$_2$), 7.1~7.5(m, 5H, PhH) |
| 52 | Me | Me | CH$_2$-(F-C$_6$H$_4$) | CMe$_2$Et | " | δ0.75(t, J=7Hz, 3H, Me), 1.25(s, 6H, CMe$_2$), 1.65(q, J=7Hz, 2H, CH$_2$), 3.00(s, 6H, NMe$_2$), 5.35(s, 2H, OCH$_2$), 6.6~7.3(m, 4H, PhH) |
| 53 | Me | Me | CH$_2$-(Cl-C$_6$H$_4$) | CMe$_2$Et | " | δ0.75(t, J=7Hz, 3H, Me), 1.25(s, 6H, CMe$_2$), 1.65(q, J=7Hz, 2H, CH$_2$), 3.00(s, 6H, NMe$_2$), 5.35(s, 2H, OCH$_2$), 7.0~7.4(m, 4H, PhH) |
| 54 | Me | Me | CH$_2$-(2-pyridyl) | CMe$_2$Et | " | δ0.75(t, J=7Hz, 3H, Me), 1.25(s, 6H, CMe$_2$), 1.65(q, J=7Hz, 2H, CH$_2$), 3.05(s, 6H, NMe$_2$), 5.50(s, 2H, OCH$_2$), 6.9~7.2(m, 1H, PyH), 7.4~7.7(m, 2H, PyH), 8.4(br.d, J=5Hz, 1H, PyH) |
| 55 | Me | Me | CH$_2$-(3-pyridyl) | CMe$_2$Et | " | δ0.75(t, J=7Hz, 3H, Me), 1.25(s, 6H, CMe$_2$), 1.65(q, J=7Hz, 2H, CH$_2$), 3.00(s, 6H, NMe$_2$), 5.40(s, 2H, OCH$_2$), 7.0~7.3(m, 1H, PyH), 7.6~7.9(m, 1H, PyH), 8.4~8.7(m, 2H, PyH) |
| 56 | Me | Me | n-C$_4$H$_9$ | CMe$_2$Et | " | δ0.7~1.9(m, 12H, Et, (CH$_2$)$_2$CH$_3$), 1.25(s, 6H, CMe$_2$), 3.00(s, 6H, NMe$_2$), 4.35(t, J=6Hz, 2H, OCH$_2$) |
| 57 | Me | Me | (CH$_2$)$_2$SCH$_3$ | CMe$_2$Et | " | δ0.75(t, J=7Hz, 3H, Me), 1.25(s, 6H, CMe$_2$), 1.65(q, J=7Hz, 2H, CH$_2$), 2.15(s, 3H, SMe), 2.85(t, J=7Hz, 2H, CH$_2$S), 3.05(s, 6H, NMe$_2$), 4.50(t, J=7Hz, 2H, OCH$_2$) |
| 58 | Me | Me | (CH$_2$)$_2$SC$_2$H$_5$ | CMe$_2$Et | Oily | δ0.75(t, J=7Hz, 3H, Me), 1.25(s, 6H, CMe$_2$), 1.25(t, J=7Hz, 3H, Me), 1.65(q, J=7Hz, 2H, CH$_2$), 2.4~2.9(m, 4H, CH$_2$SCH$_2$), 3.00(s, 6H, NMe$_2$), 4.50(t, J=7Hz, 2H, OCH$_2$) |

TABLE 1-continued (I)

$$\begin{array}{c} \text{structure with } R_1, R_2, R_3, R_4 \end{array}$$

| Compd. No. | R₁ | R₂ | R₃ | R₄ | Property or mp (°C.) | ¹H-NMR |
|---|---|---|---|---|---|---|
| 59 | Me | Me | CH₂-C₆H₅ (benzyl) | 1-Me-cyc-Pr | " | δ0.6~0.9(m, 2H, cyc-Pr), 1.0~1.3(m, 2H, cyc-Pr), 1.45(s, 3H, Me), 3.00(s, 6H, NMe₂), 5.35(s, 2H, OCH₂), 7.1~7.5(m, 5H, PhH) |
| 60 | Me | Me | CH₂-(3-F-C₆H₄) | 1-Me-cyc-Pr | " | δ0.6~0.9(m, 2H, cyc-Pr), 1.0~1.3(m, 2H, cyc-Pr), 1.45(s, 3H, Me), 3.00(s, 6H, NMe₂), 5.35(s, 2H, OCH₂), 6.8~7.3(m, 4H, PhH) |
| 61 | Me | Me | CH₂-(3-Cl-C₆H₄) | 1-Me-cyc-Pr | " | δ0.6~0.9(m, 2H, cyc-Pr), 1.0~1.3(m, 2H, cyc-Pr), 1.45(s, 3H, Me), 3.00(s, 6H, NMe₂), 5.30(s, 2H, OCH₂), 7.0~7.5(m, 4H, PhH) |
| 62 | Me | Me | (CH₂)₂SC₂H₅ | 1-Me-cyc-Pr | " | δ0.6~0.9(m, 2H, cyc-Pr), 1.0~1.3(m, 2H, cyc-Pr), 1.25(t, J=7Hz, 3H, Me), 1.40(s, 3H, Me), 2.4~3.0(m, 4H, CH₂SCH₂), 3.00(s, 6H, NMe₂), 4.45(t, J=7Hz, 2H, OCH₂) |
| 63 | Me | Me | n-C₇H₁₅ | CMe₃ | " | δ1.30(s, 9H, t-Bu), 0.7~2.0(m, 13H, C₆H₁₃), 3.00(s, 6H, NMe₂), 4.40(t, J=6Hz, 2H, OCH₂) |
| 64 | Me | Me | n-C₈H₁₇ | CMe₃ | " | δ1.30(s, 9H, t-Bu), 0.7~2.0(m, 15H, C₇H₁₅), 3.00(s, 6H, NMe₂), 4.40(t, J=6Hz, OCH₂) |
| 65 | Me | Me | n-C₉H₁₉ | CMe₃ | " | δ1.30(s, 9H, t-Bu), 0.7~2.0(m, 17H, C₈H₁₇), 3.00(s, 6H, NMe₂), 4.40(t, J=6Hz, OCH₂) |
| 66 | Me | Me | n-C₁₀H₂₁ | CMe₃ | Oily | δ1.30(s, 9H, t-Bu), 0.7~2.0(m, 19H, C₉H₁₉), 3.00(s, 6H, NMe₂), 4.40(t, J=6Hz, OCH₂) |
| 67 | Me | Me | (CH₂)₃-C₆H₅ | CMe₃ | " | δ1.30(s, 9H, t-Bu), 2.0~2.4(m, 2H, CH₂), 2.75(t, J=7Hz, 2H, CH₂Ph), 3.05(s, 6H, NMe₂), 4.40(t, J=6Hz, 2H, OCH₂), 7.10(s, 5H, PhH) |
| 68 | Me | Me | (CH₂)₂O-C₆H₅ | CMe₃ | " | δ1.30(s, 9H, t-Bu), 3.00(s, 6H, NMe₂), 4.2~4.4(m, 2H, CH₂OPh), 4.6~4.8(m, 2H, OCH₂), 6.7~7.4(m, 5H, PhH) |
| 69 | Me | Me | CH₂-(2,4-Cl₂-C₆H₃) | CMe₃ | " | δ1.30(s, 9H, t-Bu), 3.00(s, 6H, NMe₂), 5.45(s, 2H, OCH₂), 7.10(dd, J=2, 8Hz, 1H, PhH), 7.25(d, J=2Hz, 1H, PhH), 7.45(d, J=8Hz, 1H, PhH) |
| 70 | Me | Me | CH₂-(2-thienyl) | CMe₃ | " | |
| 71 | Me | Me | CH₂-(2,4-F₂-C₆H₃) | CMe₃ | " | δ1.30(s, 9H, t-Bu), 3.05(s, 6H, NMe₂), 5.35(s, 2H, OCH₂), 6.4~7.1(m, 3H, PhH) |
| 72 | Me | Me | CH₂COC₂H₅ (ester) | CMe₃ | " | δ1.30(s, 9H, t-Bu), 1.30(t, J=7Hz, 3H, Me), 3.05(s, 6H, NMe₂), 4.20(q, J=7Hz, 2H, CO₂CH₂), 4.90(s, 2H, OCH₂) |

TABLE 1-continued

Structure (I):

$$\underset{R_4}{\overset{N \longrightarrow N-\overset{O}{\overset{\|}{C}}-N\overset{R_1}{\underset{R_2}{}}}{\underset{N}{\|}}} \quad \text{(I)}$$
(with R_4 group and OR_3 on the ring)

| Compd. No. | R₁ | R₂ | R₃ | R₄ | Property or mp (°C.) | ¹H-NMR |
|---|---|---|---|---|---|---|
| 73 | Me | Me | CH₂COC₃H₉-iso (ketone) | CMe₃ | " | δ1.25(d, J=6Hz, 6H, Me₂), 1.30(s, 9H, t-Bu), 3.05(s, 6H, NMe₂), 4.80(s, 2H, OCH₂), 4.8~5.2(m, 1H, CO₂CH) |
| 74 | Me | Me | CH₂COC₄H₉-n (ketone) | CMe₃ | Oily | δ0.7~1.8(m, 7H, C₃H₇), 1.30(s, 9H, t-Bu), 3.05(s, 6H, NMe₂), 4.10(t, J=6Hz, 2H, CO₂CH₂), 4.85(s, 2H, OCH₂) |
| 75 | Me | Me | CH₂C(O)—C₆H₄—Cl | CMe₃ | 124~125 | δ1.25(s, 9H, t-Bu), 3.10(s, 6H, NMe₂), 5.55(s, 2H, OCH₂), 7.35(d, J=8Hz, 2H, PhH), 7.75(d, J=8Hz, 2H, PhH) |
| 76 | Me | Me | (CH₂)₂OC₈H₇-n | CMe₃ | Oily | δ0.90(t, J=7Hz, 3H, Me), 1.30(s, 9H, t-Bu), 1.3~1.8(m, 2H, CH₂), 3.05(s, 6H, NMe₂), 3.40(t, J=6Hz, OCH₂), 3.6~3.8(m, 2H, CH₂OPr), 4.4~4.6(m, 2H, OCH₂) |
| 77 | Me | Me | (CH₂)₃COC₂H₅ | CMe₃ | " | δ1.30(s, 9H, t-Bu), 1.30(t, J=7Hz, 3H, Me), 1.9~2.7(m, 4H, CH₂CH₂CO₂), 3.05(s, 6H, NMe₂), 4.10(q, J=7Hz, 2H, CO₂CH₂), 4.40(t, J=6Hz, 2H, OCH₂) |
| 78 | Me | Me | (CH₂)₄CN | CMe₃ | " | δ1.30(s, 9H, t-Bu), 1.7~2.1(m, 4H, CH₂CH₂), 2.3~2.6(m, 2H, CH₂CN), 3.05(s, 6H, NMe₂), 4.40(br.t, J=5Hz, 2H, OCH₂) |
| 79 | Me | Me | CH₂CH=CH—Ph | CMe₃ | " | δ1.30(s, 9H, t-Bu), 3.00(s, 6H, NMe₂), 5.00(d, J=5.5Hz, 2H, OCH₂), 6.0~6.6(m, 2H, CH=CH), 7.0~7.5(m, 5H, PhH) |
| 80 | Me | Me | CH₂S—Ph | CMe₃ | 98~99 | δ1.30(s, 9H, t-Bu), 3.00(s, 6H, NMe₂), 5.70(s, 2H, OCH₂S), 7.1~7.5(m, 5H, PhH) |

The method of preparing the compound of the present invention is now described.

The compound of the present invention (I) can be prepared according to the following general scheme. In this scheme, R₁ to R₄ are as defined above, and X represents an eliminable group such as an iodine atom, chlorine atom, and bromine atom.

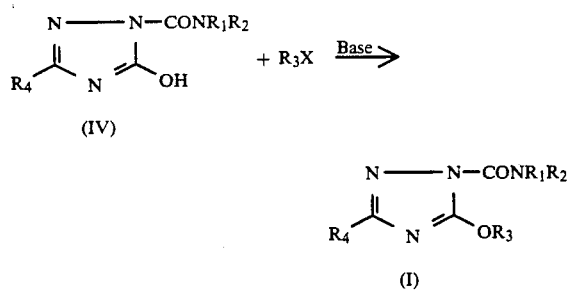

As the base to be used in the above preparation method, sodium carbonate, potassium carbonate, or a tertiary amine such as triethylamine and N,N-dimethylaniline is preferable, and the solvent, acetone, methyl ethyl ketone, tetrahydrofuran, and dimethylformamide may be employed. The reaction temperature is preferably from the reflux temperature of the solvent to 100° C.

The compound represented by the formula (IV) or tautomeric isomer thereof can be synthesized by reacting 3-t-1H-1,2,4-triazole-5-one represented by the formula (II) or tautomeric isomer thereof with an alkylcarbamoyl chloride represented by the formula (III) (where R₁, R₂ represent lower alkyl groups) in a solvent with base.

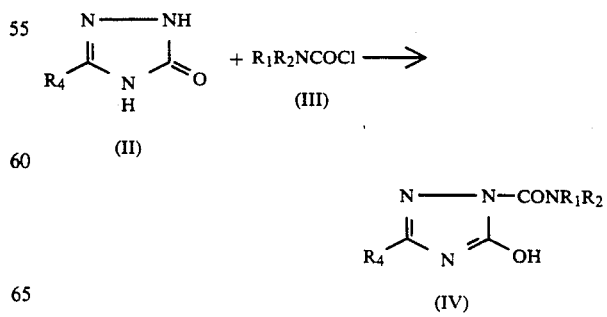

Of the compounds represented by the formula (IV), the compound in which R₁ is represented by hydrogen and $R_2$ by a lower alkyl group can be synthesized by reacting the compound (II) with a compound represented by the formula (V) (wherein $R_2$ represents a lower alkyl group) in a solvent in the presence or absence of a base.

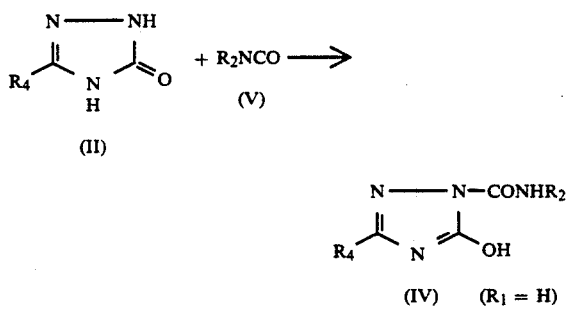

(II)     (V)

$$\underset{(IV)\quad (R_1 = H)}{\underset{R_4}{\overset{N-----N-CONHR_2}{\bigtriangleup}}\underset{N}{\phantom{x}}\overset{}{\underset{OH}{\phantom{x}}}}$$

SYNTHESIS EXAMPLES

The following are Synthesis Examples of the present invention, which in no way limit the scope of the present invention.

SYNTHESIS EXAMPLE 1

Synthesis of 5-Benzyloxy-3-tert-butyl-1,N,N-dimethylcarbamoyl-1,2,4-triazole 1-1. Synthesis of 3-tert-butyl-1H-1,2,4-triazole-5-one To 111.5 g (1 mole) of semicarbazide hydrochloride was added an aqueous sodium hydroxide solution of 80 g (2 moles) of sodium hydroxide dissolved in 300 ml of water, and 300 ml of 1,4-dioxane. After the semicarbazide hydrochloride was completely dissolved, the reaction vessel was cooled to a solution temperature of 20° C. or lower, and to the solution was added dropwise 121 g (1 mole) of trimethylacethyl chloride with stirring, maintaining the reaction temperature of 20° C. or lower. After the addition was completed the reaction mixture was kept in the room temperature, and stirring was continued for additional 2 hours. The white precipitates of trimethylacetylsemicarbazide formed were collected by filtration, washed with water, and then dried.

To the obtained white powder of trimethylacetylsemicarbazide was added 1500 ml of a 5% aqueous potassium hydroxide solution, and the mixture was heated to 100° C. with stirring. After the contents were completely dissolved, the solution was further heated at 100° C. for one hour, and the reaction mixture was cooled and then neutralized by an addition of conc. hydrochloric acid. The white precipitates formed were collected by filtration, washed with water, and then dried under reduced pressure to give 64 g of 3-tert-butyl-1H-1,2,4-triazole-5-one as white powder (yield 45%).

1-2. Synthesis of 3-tert-butyl-1-N,N-dimethylcarbamoyl-5-hydroxy-1,2,4-triazole

To a mixture of 3-tert-butyl-1H-1,2,4-triazole-5-one 50 g (0.36 mole), triethylamine 43 g (0.43 mole), 4-N,N-dimethylaminopyridine 1.0 g (0.008 mole) was added 500 ml of tetrahydrofuran, and to the resultant mixture was added, 41.9 g (0.39 mole) of N,N-dimethylcarbamoyl chloride with stirring, and the mixture was heated under reflux for 3 hours. The reaction mixture was left to cool to room temperature, the triethylamine hydrochoride formed was removed by filtration, and the solution was left to stand, with an addition of 40 ml of conc. hydrochloric acid, for 2 hours.

The solution was poured into ice-water and then neutralized with addition of 4N aqueous sodium hydroxide solution, the aqueous solution was extracted with ethyl acetate and then with methylene chloride, and the organic phases obtained were combined and dried over anhydrous sodium sulfate. Then, by concentrating the solution under a reduced pressure, white solid was obtained. This white solid was washed with n-hexane, whereby 70.3 g of 3-tert-butyl-1-N,N-dimethylcarbamoyl-5-hydroxy-1,2,4-triazole was obtained as a white powder (yield 93%).

1-3. Synthesis of 5-benzyloxy-3-tert-butyl-1-N,N-dimethylcarbamoyl-1,2,4-triazole To a mixture of 3-tert-butyl-N,N-dimethylcarbamoyl-5-hydroxy-1,2,4-triazole 4.24 g (0.02 mole) and potassium carbonate 4.14 g (0.03 mole) was added 100 ml of acetone, and to the mixture was added 4.10 g (0.024 mole) of benzyl bromide, and the mixture was heated under reflux for 2 hours with stirring. After the reaction mixture was concentrated under a reduced pressure, the residue obtained was diluted with water and extracted with methylene chloride. The organic phase was dried over anhydrous sodium sulfate, then concentrated under a reduced pressure, and the colorless oily substance obtained was subjected to silica gel column chromatography and eluted with a solvent mixture of 1:1 of ethyl acetate, n-hexane, whereby a white solid of 5-benzyloxy-3-tert-butyl-1-N,N-dimethylcarbamoyl-1,2,4-triazole was obtained. This was further recrystallized from n-hexane to obtain 2.30 g of white crystals (yield 38%).

SYNTHESIS EXAMPLE 2

Synthesis of 3-tert-butyl-1-N,N-dimethylcarbamoyl-5-isopropoxy-1,2,4-triazole

To a mixture of 3-tert-butyl-1-N,N-dimethylcarbamoyl-5-hydroxy-1,2,4-triazole 4.24 g (0.02 mole) and potassium carbonate 4.14 g (0.03 mole) was added 100 ml of N,N-dimethylformamide. Then to the mixture was added, 5.10 g (0.03 mole) of 2-iodopropane with stirring, and heating and stirring were continued at 90° C. for 10 hours. The solvent was removed under a reduced pressure, and the residue then diluted with water and extracted with ethyl acetate. The organic phase was collected, washed with water and then with saturated aqueous sodium chloride, and dried over anhydrous sodium sulfate. The extract was concentrated under a reduced pressure, and then the product obtained was subjected to silica gel column chromatography and eluted with a solvent mixture of 1:1 of ethyl acetate, n-hexane to give 3.50 g of 3-tert-butyl-1-N,N-dimethylcarbamoyl-5-isopropoxy-1,2,4-triazole as a colorless oily substance (yield 69%).

SYNTHESIS EXAMPLE 3

Synthesis of 5-benzyloxy-3-tert-butyl-1-N-methylcarbamoyl-1,2,4-triazole

3-1. Synthesis of 3-tert-butyl-1-N-methylcarbamoyl-5-hydroxy-1,2,4-triazole

To a mixture of 3-tert-butyl-1H-1,2,4-triazole-5-one 14.1 g (0.1 mole) triethylamine 5 g (0.05 mole) was added 500 ml of tetrahydrofuran. Then to the mixture was added, while stirring, 11.4 g (0.2 mole) of methyl isocyanate, and heating and stirring were continued at 60° C. for 2 hours.

After the reaction was completed, the reaction mixture was concentrated under a reduced pressure to give white precipitates. The white precipitates were collected by filtration and washed with n-hexane to give 16.0 g of 3-tert-butyl-1-N-methylcarbamoyl-5-hydroxy-1,2,4-triazole as a white powder (yield 81%).

3-2. Synthesis of 5-benzyloxy-3-tert-butyl-1-N-methylcarbamoyl-1,2,4-triazole To a mixture of 3-tert-butyl-1-N-methylcarbamoyl-5-hydroxy-1,2,4-triazole 5.94 g (0.03 mole) and potassium carbonate 6.21 g (0.045 mole) was added 100 ml of methyl-ethyl ketone. Then to the mixture was added, while stirring, 4.17 g (0.033 mole) of benzyl chloride, and the mixture was heated under reflux for 2 hours. After the reaction mixture was concentrated under a reduced pressure, the residue obtained was diluted with water and extracted with methylene chloride. The organic phase was dried over anhydrous sodium sulfate, and then concentrated under a reduced pressure, and the pale yellow oily substance obtained was subjected to silica gel column chromatography and eluted with a solvent mixture of 1:2 of ethyl acetate and n-hexane, to give 0.3 g of 5-benzyloxy-3-tert-butyl-1-N-methylcarbamoyl- 1,2,4-triazole as a white solid (yield 3.5%).

The insecticide composition of the present invention exhibits excellent effects against Hemiptera such as aphids, Diptera such as flies and mosquitoes, Nematoidea such as root-knot nemadode, and Pseudonematoidea such as great nematode. Examples of harmful insects are shown below, but the harmful insects against which the present compounds are effective are not limited thereto.

These insects, include Coleoptera injurious insects such as:
Anomala rufocuprea,
Callosobruchus chinemsis,
Sitophilus zeawais,
Epilachna vigintioctomaculata,
Lissorhoptrus oryzophilus;
Hemiptera harmful insects such as:
Laodelphox striatellus,
Nilaparvata lugens,
Sogatella furcifera,
Nephotettix cincticeps,
Nezara amtennata,
Trialeurodes vaporariorum,
Unaspis yanoneusis,
Aphis gossypii,
Myzus persicae,
Aulacorthum solani,
Rhopa pseudobrassicae;
Diptera injurious insects such as:
Musca domestica,
Aedes aegypti,
Culex pipiens;
Orthoptera injurious insects such as:
Blatella germanica,
Periplaneta americana,
Locuota migratoria;
Isoptera injurious insects such as:
Copto termes formosawis;
Lepidoptera injurious insects such as:
Pieris rapae,
Plutella xylostella,
Mamestra brassicae,
Spodoptera litura,
Heliothis virescens,
Agrotis fucosa,
Chilo suppressalis, etc.

As mites, there are included, for example:
*Tetranychus urticae, Panonychus citri,* and *Aculops pelekassi.*

When the insecticide of the present invention is practically applied, it can be used alone without the addition of other components, but to make it more readily useable as a control medicine, it is generally formulated with a carrier to make a preparation which is diluted, if necessary, before use. When forming the preparation of the insecticide of the present invention, no special conditions are required, and it can be formed into any desired dosage form such as an emulsion, wettable powder, powder, or granules according to the methods generally well known in the art of agricultural medicines. The carrier may include inorganic materials such as clays, talc, bentonite, calcium carbonate, diatomaceous earth, zeolite, and anhydrous silicic acid; vegetable organic materials such as wheat, starch, and crystalline cellulose; polymeric compounds such as petroleum resin, polyvinyl chloride, and polyalkylene glycol, urea; waxes; and so on. As the liquid carrier, various oils, organic solvents and water may be included. Further, auxiliary agents such as humectants, dispersing agents, binders, and spreaders can be used if desired, either alone or in combination. As the auxiliary agent to be used for the purpose of wetting, dispersion, spreading, component stabilization, and rust prevention, there may be included various surfactants, polymeric compounds such as gelatin, albumin, sodium alginate, methyl cellulose, carboxymethyl cellulose, polyvinyl alcohol, xanthan gum, and other auxiliary agents. As the surfactant, there may be included nonionic surfactants such as those having ethylene oxide polymerized to alkylphenol, higher alcohol, alkylnaphthol, higher fatty acid, fatty acid ester, and dialkylphosphoric acid amine, or those having ethylene oxide and propylene oxide polymerized, anionic surfactants, for example, alkylsulfates such as sodium laurylsulfate, alkylsulfonates such as sodium 2-ethylhexylsulfonate, arylsulfonates such as sodium ligninsulfonate, and sodium dodecylbenzenesulfonate, and various cationic and amphoteric surfactants.

The insecticide of the present invention can be mixed with another physiologically active substance, to provide a multi-purpose agricultural medicine. As the physiologically active substance, insecticides and acaricides are well known, and sterilizers, nematocides, herbicides, plant growth regulators, fertilizers, BT agents, nucleus polygonal virus, and insect growth regulators or hormone agents can be used. Specific examples of these physiologically active substances are shown below.

Pyrethloid and pyrethloid complex compounds such as etofenblocs [2-(4-ethoxyphenyl)-2-methylpropyl 3-phenoxybenzyl ether], phenvalerate [3-phenoxy-α-cyanobenzyl-α-isopropyl-4-chlorophenylacetate], permesulin [3-phenoxybenzyl 3-(2,2-dichlorovinyl)-2,2-dibromovinyl)-1-carboxylic acid ester], sipermesulin [3-phenoxy-α-cyanobenzyl 3-(2,2-chlorovinyl)-2,2-dimethylcyclopropane-1-carboxylic acid deltamesulin [3-phenoxy-α-cyanobenzyl 3-(2,2-ester], dibromovinyl)-2,2-dimethylcyclopropane-1-carboxylic acid ester], or insect flower extract.

Organic phosphorus type insecticides such as pyridaphenthion (o,o-diethyl-o-(3-oxo-2N-phenyl-2H-pyridazin-6-yl)phosphorothioate], DDVP [o,o-dimethyl-o-(2,2-dichlorovinyl)phosphate], and phenitrothion [o,o-dimethyl-o-(3-methyl-4-nitrophenyl)phosphorothioate].

Carbamate type insecticides such as NAC [1-naphthyl-N-methylcarbamate], MTMC [meta-tolyl-N-methylcarbamate], and pyrimer [2-dimethylamino-5,6-dimethylpyrinidin-4-yl dimethylcarbamate].

Integumen formation inhibitors such as pupurofedin [2-tert-butylimino-3-isopropyl-5-phenyl-3,4,5,6-tetrahydro-2H-1,3,5-thiadiazin-4-one], and CME 134 [1-(3,5-dichloro-2,4-difluorophenyl)-3-(2,6-difluorobenzoyl)urea].

Sterilizers such as fusaride [4,5,6,7-tetrachlorophthalide], IBP [S-benzyl diisopropylphosphorothioate], EDDP [o-ethyl diphenylphosphorothioate], benomil [methyl 1-(butylcarbamoyl)-2-benzimidazole carbamate], probenazol [3-allyloxy-1,2-benzisothiazole-1,1-dioxide], isoprothiolan [diisopropyl-1,3-dithiolan-2-ylidene malonate], and tricyclazol [5-methyl-1,2,4-triazolo(3,4-b)benzothiazole].

Acaricides such as kensen [2,2,2-trichloro-1,1,-bis(p-chlorophenyl)ethanol], amitraz [3-methyl-1,5-bis(2,4-xylyl)-1,3,5-triazapenta-1,4-diene], and tricyclohexyltin hydroxide.

The active ingredient in the insecticide of the present invention is preferably contained at 0.001 to 95% by weight, more preferably 0.1 to 70% by weight.

PREPARATION EXAMPLES

Preparation Examples of the insecticide of the present invention are now shown, but the present invention is in no way limited thereto.

PREPARATION EXAMPLE 1: POWDER

A mixture of 3 parts by weight of the compound of the present invention, 10 parts by weight of Carplex #80 [white carbon, Shionogi Seiyaku K.K.], and 87 parts by weight of clay was crushed to obtain 100 parts by weight of a powder containing 3% by weight of the active ingredient.

PREPARATION EXAMPLE 2: POWDER

A mixture of 0.5 part by weight of the compound of the present invention, 49.5 parts by weight of calcium carbonate, and 50 parts by weight of clay was crushed to obtain 100 parts by weight of a powder containing 0.5% by weight of the active ingredient.

PREPARATION EXAMPLE 3: WETTABLE POWDER

An amount of 50 parts by weight of the compound of the present invention, 5 parts by weight of Solpol [surfactant, produced by Toho Kagaku K.K.] and 45 parts by weight of Radiolite [calcined diatomaceous earth, produced by Showa Kagaku K.K.] were uniformly crushed and mixed to obtain 100 parts by weight of a wettable powder containing 50% by weight of the active ingredient.

PREPARATION EXAMPLE 4: WETTABLE POWDER

An amount of 10 parts by weight of the compound of the present invention, 10 parts by weight of Carplex #8 white carbon, produced by Shionogi Seiyaku K.K.], 3 parts by weight of Emal 10 [surfactant, produced by Kao K.K.] and 77 parts by weight of clay were uniformly crushed and mixed to obtain 100 parts by weight of a wettable powder containing 10% by weight of the active ingredient.

PREPARATION EXAMPLE 5: GRANULE

One part by weight of the compound of the present invention, 2 parts by weight of sodium dodecylbenzenesulfonate, 1 part by weight of sodium ligninsulfonate, 25 parts by weight of talc, and 71 parts by weight of bentonite were uniformly mixed, kneaded with an addition of water, and then granulated by an extrusion granulator and dried, to obtain 100 parts by weight of granules containing 1% by weight of the active ingredient.

PREPARATION EXAMPLE 6: GRANULE

Three parts by weight of the compound of the present invention, 3 parts by weight of carboxymethyl cellulose, 2 parts by weight of sodium ligninsulfonate, and 92 parts by weight of clay were uniformly mixed, kneaded with an addition of water, then granulated by an extrusion granulator and dried, to obtain 100 parts by weight of granules containing 3% by weight of the active ingredient.

PREPARATION EXAMPLE 7: MIXED WETTABLE POWDER

An amount of 20 parts by weight of the compound of the present invention, 10 parts by weight of etofenblocs, 5 parts by weight of Solpol [surfactant, produced by Toho Kagaku K.K.] and 65 parts by weight of Radiolite (calcined diatomaceous earth, produced by Showa Kagaku K.K.) were uniformly mixed to obtain 100 parts by weight of a mixed wettable powder containing 20% by weight of the compound of the present invention and 10% by weight of etofenblocs, respectively.

TEXT EXAMPLES

The control effect of the compound of the present invention is now described in detail with reference to biological test examples.

TEST EXAMPLE 1

Insecticidal Effect Against *Nephotettix cinticeps*

The prepared wettable powder of the compound of the present invention was diluted with water to form an adjusted to 500 ppm of the active ingredient. This solution was sprayed onto rice seedlings in the 3- to 4-leaf stage and planted in a pot, and after air drying, the pot was covered with a cylinder of acrylic resin. Then 10 adult female insects, *Neophettix cinticeps*, were introduced into the covered pot, and after 2 days, the number of dead insects was determined and the mortality calculated. The results are shown in Table 2.

TABLE 2

| Compound No. | Mortality (%) 500 ppm |
|---|---|
| 1 | 100 |
| 2 | 95 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 95 |
| 13 | 100 |
| 14 | 100 |
| 15 | 100 |
| 16 | 100 |
| 17 | 100 |
| 18 | 100 |
| 19 | 100 |
| 20 | 100 |
| 21 | 100 |
| 22 | 100 |
| 23 | 100 |
| 24 | 100 |
| 25 | 100 |
| 26 | 100 |
| 27 | 100 |
| 28 | 100 |
| 29 | 100 |
| 30 | 100 |
| 31 | 100 |
| 32 | 100 |
| 33 | 100 |
| 34 | 100 |
| 35 | 100 |
| 36 | 100 |
| 37 | 100 |
| 38 | 100 |
| 39 | 100 |
| 40 | 100 |
| 41 | 100 |
| 42 | 100 |
| 43 | 100 |
| 44 | 100 |
| 45 | 100 |
| 46 | 100 |
| 47 | 100 |
| 48 | 100 |
| 49 | 100 |
| 50 | 100 |
| 51 | 100 |
| 52 | 95 |
| 53 | 100 |
| 54 | 100 |
| 55 | 100 |
| 56 | 100 |
| 57 | 100 |
| 58 | 100 |
| 59 | 100 |
| 60 | 100 |
| 61 | 100 |
| 62 | 100 |
| 63 | 100 |
| 64 | 100 |
| 65 | 100 |
| 66 | 100 |
| 67 | 100 |
| 68 | 100 |
| 69 | 100 |
| 70 | 100 |
| 71 | 100 |
| 72 | 100 |
| 73 | 100 |
| 74 | 100 |
| 75 | 100 |
| 76 | 100 |
| 77 | 100 |
| 78 | 100 |
| 79 | 100 |
| 80 | 100 |
| Comparative agent[*1] | 20 |
| Control agent[*2] | 100 |

[*1] 2-secondary-butylphenyl-N-methylcarbamate (Bassa ®)
[*2] 1-dimethylcarbamoyl-3-tert-butyl-5-carboethoxymethylthio-1H-1,2,4-triazole (Japanese Unexamined Patent Publication 62-70365)

TEST EXAMPLE 2

Insecticidal Effect Against *Laodelphax stritellusa*

The prepared wettable powder of the compound present invention was diluted with water to form an adjusted to 500 ppm of the active ingredient. A constant volume of this solution was injected into the soil in a pot in which rice seedlings of the 3- to 4-leaf stage were planted, and one day later, the pot surface was covered in such a way that the cover was not in contact with the chemicals, and 14 *Laodelphax striatellus* larvae, 14 days old, were introduced therein. After 2 days, the number of dead insects was determined, and the mortality was calculated. The results are shown in Table 3.

TABLE 3

| Compound No. | Mortality (%) 500 ppm |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 15 | 100 |
| 16 | 100 |
| 17 | 100 |
| 18 | 100 |
| 19 | 100 |
| 20 | 100 |
| 21 | 100 |
| 22 | 100 |
| 23 | 100 |
| 24 | 90 |
| 25 | 100 |
| 26 | 100 |
| 27 | 100 |
| 28 | 100 |
| 29 | 100 |
| 30 | 100 |
| 31 | 100 |
| 32 | 100 |
| 33 | 100 |
| 34 | 100 |
| 35 | 100 |
| 36 | 100 |
| 37 | 100 |
| 38 | 100 |
| 39 | 100 |
| 40 | 100 |
| 41 | 100 |
| 42 | 100 |
| 43 | 100 |
| 44 | 100 |
| 45 | 100 |
| 46 | 100 |
| 47 | 100 |
| 48 | 100 |
| 49 | 100 |
| 50 | 100 |
| 51 | 100 |

TABLE 3-continued

| Compound No. | Mortality (%) 500 ppm |
|---|---|
| 52 | 100 |
| 53 | 100 |
| 54 | 100 |
| 55 | 100 |
| 56 | 100 |
| 57 | 100 |
| 58 | 100 |
| 59 | 100 |
| 60 | 100 |
| 61 | 100 |
| 62 | 100 |
| 63 | 100 |
| 64 | 100 |
| 65 | 100 |
| 66 | 100 |
| 67 | 100 |
| 68 | 100 |
| 69 | 100 |
| 70 | 100 |
| 71 | 100 |
| 72 | 100 |
| 73 | 100 |
| 74 | 100 |
| 75 | 100 |
| 76 | 100 |
| 77 | 100 |
| 78 | 100 |
| 79 | 100 |
| 80 | 100 |
| Comparative agent | 0 |
| Control agent | 100 |

TEST EXAMPLE 3

Insecticidal Effect Against *Aphis gossypii*

The prepared wettable powder of the compound present invention was diluted with water to form a solution containing 500 ppm of the active ingredient. A constant volume of the chemical solution was sprayed onto a pot in which cucumber young seedlings previously inoculated with *Aphis gossypii* were planted. After 1 day, the number of aphid insects alive on the leaf surfaces was determined, and the Mortality was calculated from the number of the insects provided before the treatment. The results are shown in Table 4.

TABLE 4

| Compound No. | Mortality (%) 500 ppm |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 15 | 100 |
| 16 | 100 |
| 17 | 100 |
| 18 | 100 |
| 19 | 100 |
| 20 | 100 |
| 21 | 100 |
| 22 | 100 |
| 23 | 100 |
| 24 | 100 |
| 25 | 100 |
| 26 | 100 |
| 27 | 100 |
| 28 | 100 |
| 29 | 100 |
| 30 | 100 |
| 31 | 100 |
| 32 | 100 |
| 33 | 100 |
| 34 | 100 |
| 35 | 100 |
| 36 | 100 |
| 37 | 100 |
| 38 | 100 |
| 39 | 100 |
| 40 | 100 |
| 41 | 100 |
| 42 | 100 |
| 43 | 100 |
| 44 | 100 |
| 45 | 100 |
| 46 | 100 |
| 47 | 100 |
| 48 | 100 |
| 49 | 100 |
| 50 | 100 |
| 51 | 100 |
| 52 | 100 |
| 53 | 100 |
| 54 | 100 |
| 55 | 100 |
| 56 | 100 |
| 57 | 100 |
| 58 | 100 |
| 59 | 100 |
| 60 | 100 |
| 61 | 100 |
| 62 | 100 |
| 63 | 100 |
| 64 | 100 |
| 65 | 100 |
| 66 | 100 |
| 67 | 100 |
| 68 | 100 |
| 69 | 100 |
| 70 | 100 |
| 71 | 100 |
| 72 | 100 |
| 73 | 100 |
| 74 | 100 |
| 75 | 100 |
| 76 | 100 |
| 77 | 100 |
| 78 | 100 |
| 79 | 100 |
| 80 | 100 |
| Comparative agent | 48 |
| Control agent[*1] | 100 |

[*1] O,S-dimethyl-N-acetylphosphoroamide thioate (Oltran ®)

TEST EXAMPLE 4

Insecticidal Effect Against *Myzus persicae*

The prepared wettable powder of the compound present invention was diluted with water to form a solution containing 500 ppm of the active ingredient. A constant volume of the chemical solution was injected into the soil in a pot in which cabbage young seedlings were previously inoculated with *Muzus persicae*. After 4 days, the number of aphid insects alive on the leaf surfaces was determined, and the Mortality was calculated from the number of the insects provided before the treatment. The results are shown in Table 5.

No Phytotoxity from any of the compounds was observed.

TABLE 5

| Compound No. | Mortality (%) 500 ppm |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 15 | 100 |
| 16 | 100 |
| 17 | 100 |
| 18 | 100 |
| 19 | 100 |
| 20 | 100 |
| 21 | 100 |
| 22 | 100 |
| 23 | 100 |
| 24 | 100 |
| 25 | 100 |
| 26 | 100 |
| 27 | 100 |
| 28 | 100 |
| 29 | 100 |
| 30 | 100 |
| 31 | 100 |
| 32 | 100 |
| 33 | 100 |
| 34 | 100 |
| 35 | 100 |
| 36 | 100 |
| 37 | 100 |
| 38 | 100 |
| 39 | 100 |
| 40 | 100 |
| 41 | 100 |
| 42 | 100 |
| 43 | 100 |
| 44 | 100 |
| 45 | 100 |
| 46 | 100 |
| 47 | 100 |
| 48 | 100 |
| 49 | 100 |
| 50 | 100 |
| 51 | 100 |
| 52 | 100 |
| 53 | 100 |
| 54 | 100 |
| 55 | 100 |
| 56 | 100 |
| 57 | 100 |
| 58 | 100 |
| 59 | 100 |
| 60 | 100 |
| 61 | 100 |
| 62 | 100 |
| 63 | 100 |
| 64 | 100 |
| 65 | 100 |
| 66 | 100 |
| 67 | 100 |
| 68 | 100 |
| 69 | 100 |
| 70 | 100 |
| 71 | 100 |
| 72 | 100 |
| 73 | 100 |
| 74 | 100 |
| 75 | 100 |
| 76 | 100 |
| 77 | 100 |
| 78 | 100 |
| 79 | 100 |
| 80 | 100 |
| Comparative agent*[1] | 53 |
| Control agent*[2] | 100 |

*[1] 1-dimethylcarbamoyl-3-3-butyl-5-carboxy-methylthio-1H-1,2,4-triazole (see Japanese Unexamined Patent Publication (Kokai) No. 62-70365)
*[2] O,S-dimethyl-N-acetylphosphoroamide thioate (Oltran ®)

TEST EXAMPLE 5

Insecticidal Effect Against *Musca domestica*

The compound of the present invention was diluted with acetone to form a solution containing 100 ppm of the active ingredient.

One ml of the acetone solution of chemicals was added dropwise in a glass laboratory dish 9 cm in diameter and dried in air. After the air drying, 15 adult female insects, Musca domestica, were introduced onto the laboratory dish, and the dish was left to stand in a thermostatic chamber at 25° C. After 24 hours, the number of dead insects was determined and the Mortality calculated therefrom to obtain the results shown in Table 6.

TABLE 6

| Compound No. | Mortality (%) 100 ppm |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 15 | 100 |
| 16 | 100 |
| 17 | 100 |
| 18 | 100 |
| 19 | 100 |
| 20 | 100 |
| 21 | 100 |
| 22 | 100 |
| 23 | 100 |
| 24 | 100 |
| 25 | 100 |
| 26 | 100 |
| 27 | 100 |
| 28 | 100 |
| 29 | 100 |
| 30 | 27 |
| 31 | 86 |
| 32 | 98 |
| 34 | 32 |
| 36 | 100 |
| 37 | 100 |
| 38 | 88 |
| 39 | 31 |
| 40 | 93 |
| 42 | 53 |
| 43 | 85 |
| 44 | 52 |
| 45 | 90 |
| 46 | 50 |
| 47 | 47 |
| 48 | 40 |
| 50 | 62 |
| 51 | 83 |
| 52 | 82 |
| 53 | 61 |

TABLE 6-continued

| Compound No. | Mortality (%) 100 ppm |
|---|---|
| 54 | 86 |
| 55 | 70 |
| 56 | 100 |
| 57 | 100 |
| 58 | 93 |
| 59 | 35 |
| 60 | 38 |
| 61 | 67 |
| 62 | 100 |
| 63 | 100 |
| 64 | 45 |
| 65 | 38 |
| 66 | 25 |
| 67 | 40 |
| 68 | 95 |
| 70 | 100 |
| 71 | 95 |
| 72 | 100 |
| 73 | 95 |
| 74 | 98 |
| 76 | 100 |
| 77 | 100 |
| 78 | 100 |
| 79 | 100 |
| 80 | 100 |
| Comparative agent | 97 |
| Control agent[*1] | 100 |

[*1] O,S-dimethyl-O-(3-methyl-4-nitrophenyl)thio-phosphate (Sumithion ®);

TEXT EXAMPLE 6

Insecticidal Effect Against Plant Parasitic Nematode

Using granules, the compound of the present invention prepared was mixed uniformly with soil, incorporated with southern root-knot nematode, packed in a 1/5000 Wagner pot, to an extent such that the active ingredient was contained in an amount of 3 kg per 10 a.

One day after mixing, five grains of cucumber seeds were seeded, and the formation ratio formed at the cucumber root portion (root-knot index) three weeks thereafter was examined. The Protected ratio root-knot information was calculated according to the following formula, to obtain the results shown in Table 7.

$$\text{Protected ratio (\%)} = \frac{\text{Sum of root-knot indices at each root}}{4 \times \text{number of examined roots}} \times 100$$

TABLE 7

| Compound No. | Protected ratio (%) |
|---|---|
| 10 | 100 |
| 11 | 100 |
| 12 | 100 |
| 13 | 100 |
| 14 | 100 |
| 16 | 50 |
| 17 | 40 |
| 20 | 50 |
| 21 | 40 |
| 22 | 100 |
| 23 | 90 |
| 25 | 50 |
| 27 | 100 |
| 28 | 95 |
| 30 | 50 |
| 31 | 100 |
| 32 | 50 |
| 33 | 60 |
| 34 | 88 |
| 35 | 95 |
| 36 | 95 |

TABLE 7-continued

| Compound No. | Protected ratio (%) |
|---|---|
| 37 | 94 |
| 38 | 50 |
| 39 | 43 |
| 41 | 85 |
| 42 | 85 |
| 43 | 90 |
| 45 | 92 |
| 47 | 40 |
| 48 | 25 |
| 49 | 100 |
| 51 | 100 |
| 52 | 100 |
| 53 | 100 |
| 54 | 80 |
| 55 | 90 |
| 56 | 100 |
| 57 | 100 |
| 58 | 80 |
| 59 | 35 |
| 61 | 100 |
| 62 | 56 |
| 63 | 75 |
| 64 | 90 |
| 65 | 70 |
| 66 | 40 |
| 67 | 60 |
| 69 | 100 |
| 70 | 100 |
| 71 | 100 |
| 72 | 100 |
| 73 | 100 |
| 74 | 100 |
| 75 | 100 |
| 76 | 100 |
| 77 | 100 |
| 78 | 100 |
| 79 | 100 |
| 80 | 100 |
| Comparative agent[*1] | 0 |
| Control agent [*2] | 100 |

[*1] 1-dimethylcarbamoyl-3-3-butyl-5-carboxymethyl-thio-1H-1,2,4-triazole (see Japanese Unexamined Patent Publication (Kokai) No. 62-70365)
[*2] N,N-dimethyl-methylcarbamoyl-oxyimino-methyl-acetamide (Bidate ®)

As apparent from the above test results, the compound of the present invention has a chemical structure different from the triazole type insecticide of the prior art, and has an excellent insecticidal spectrum and insecticidal performance.

Specifically, the compound exhibits a particularly excellent insecticidal effect against harmful insects of Diptera, Hemiptera, Nematoidea, Pseudonematoidea.

TEST EXAMPLE 7

The prepared wettable powder of the compound of the present invention was diluted with water to form a solution containing 100 ppm of the active ingredient, and a sufficient amount of the chemical solution was sprayed onto cabbage young seedlings previously inoculated with Myzus persicae. After one day, the number of aphids still alive on the leaf surfaces was determined, and the Mortality was calculated from the number of insects provided before the treatment. The results are shown in Table 8.

TABLE 8

| Compound No. | Mortality (%) 100 ppm |
|---|---|
| 1 | 98 |
| 2 | 93 |
| 3 | 93 |
| 4 | 100 |
| 5 | 88 |
| 6 | 100 |

TABLE 8-continued

| Compound No. | Mortality (%) 100 ppm |
|---|---|
| 7 | 100 |
| 8 | 100 |
| 9 | 100 |
| 10 | 80 |
| 11 | 99 |
| 12 | 100 |
| 13 | 92 |
| 14 | 100 |
| 15 | 88 |
| 16 | 100 |
| 17 | 94 |
| 18 | 100 |
| 20 | 100 |
| 21 | 100 |
| 22 | 100 |
| 23 | 100 |
| 24 | 92 |
| 25 | 100 |
| 26 | 100 |
| 27 | 100 |
| 28 | 100 |
| 29 | 100 |
| 30 | 78 |
| 31 | 100 |
| 32 | 100 |
| 33 | 90 |
| 34 | 100 |
| 35 | 100 |
| 36 | 100 |
| 37 | 100 |
| 38 | 100 |
| 39 | 100 |
| 40 | 92 |
| 41 | 94 |
| 42 | 98 |
| 43 | 99 |
| 45 | 100 |
| 46 | 100 |
| 47 | 100 |
| 48 | 100 |
| 49 | 100 |
| 51 | 100 |
| 52 | 100 |
| 53 | 100 |
| 54 | 100 |
| 55 | 100 |
| 56 | 96 |
| 57 | 100 |
| 58 | 100 |
| 59 | 100 |
| 60 | 100 |
| 61 | 100 |
| 62 | 100 |
| 63 | 100 |
| 64 | 100 |
| 65 | 100 |
| 66 | 92 |
| 67 | 93 |
| 68 | 82 |
| 70 | 100 |
| 71 | 100 |
| 72 | 100 |
| 73 | 100 |
| 74 | 100 |
| 75 | 100 |
| 76 | 100 |
| 77 | 100 |
| 78 | 100 |
| 79 | 100 |

TABLE 8-continued

| Compound No. | Mortality (%) 100 ppm |
|---|---|
| 80 | 100 |

We claim:

1. A triazole compound represented by the formula (I):

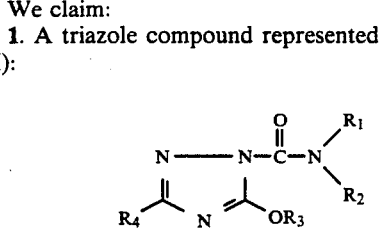

wherein $R_1$ represents hydrogen or a $C_1$-$C_2$ alkyl group, $R_2$ represents a $C_1$-$C_2$ alkyl group, $R_3$ represents a $C_1$-$C_{12}$ alkyl group, a $C_1$-$C_{12}$ alkenyl group, a $C_4$-$C_7$ cycloalkylmethyl group, a $C_1$-$C_{12}$ haloalkyl group, a $C_1$-$C_6$ alkyl group substituted with a phenyl group (which may be also substituted with a halogen atom, a $C_1$-$C_6$ alkyl group, a $C_1$-$C_6$ haloalkyl group, a $C_1$-$C_6$ alkoxy group or a $C_1$-$C_6$ haloalkoxy group), a $C_1$-$C_6$ hydroxyalkyl group, a $C_1$-$C_6$ thioxyalkyl group or a $C_1$-$C_6$ carbonylalkyl group, a $C_1$-$C_6$ alkyl group substituted with a $C_1$-$C_6$ alkoxy group or a $C_1$-$C_6$ alkylthio group, a $C_1$-$C_6$ alkyl group substituted with a $C_1$-$C_6$ alkylsulfinyl group or a $C_1$-$C_6$ alkyl-sulfonyl group, a $C_1$-$C_6$ alkyl group substituted with an $\alpha$- or $\beta$-thienyl group (which may be also substituted with a halogen atom), a $C_1$-$C_6$ alkyl group substituted with a cyano group or a $C_1$-$C_6$ alkyl group substituted with a $C_2$-$C_7$ alkoxycarbonyl group, $R_4$ represents

(where $R_5$, $R_6$ and $R_7$ represent the same or different $C_1$-$C_3$ alkyl groups, or in some cases, two groups of $R_5$, $R_6$ and $R_7$ form a $C_3$-$C_5$ carbon ring).

2. A triazole compound according to claim 1, wherein $R_1$, $R_2$ represent the same or different lower alkyl groups, $R_3$ represents a straight or branched alkyl group or alkenyl group, a cyclopropylmethyl group, an alkoxylalkyl group, or a benzyl group or a phenethyl group which may be also substituted, and $R_4$ represents a t-butyl group.

3. A triazole compound according to claim 2, wherein $R_1$ and $R_2$ each represent a methyl group.

4. An insecticide composition comprising an insecticidally effective amount of a triazole compound according to claim 1 as the active ingredient, and a carrier therefor.

5. An insecticide composition comprising an insecticidally effective amount of a triazole compound according to claim 2 as the active ingredient, and a carrier therefor.

6. An insecticide composition according to claim 5, wherein $R_1$ and $R_2$ are each a methyl group.

* * * * *